United States Patent
Goldenberg et al.

(10) Patent No.: US 6,440,416 B1
(45) Date of Patent: Aug. 27, 2002

(54) VACCINES AGAINST CANCER AND INFECTIOUS DISEASES

(75) Inventors: David M. Goldenberg, Short Hills; Hans J. Hansen, Westfield, both of NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 08/183,381

(22) Filed: Jan. 2, 1992

Related U.S. Application Data

(63) Continuation of application No. 07/470,637, filed on Jan. 26, 1990, now abandoned.

(51) Int. Cl.⁷ ............... A61K 39/395; A61K 39/42; A61K 39/40; C07K 16/00
(52) U.S. Cl. ............... 424/131.1; 424/138.1; 424/148.1; 424/160.1; 424/164.1; 424/151.1; 530/387.2; 530/387.7; 530/388.3; 530/388.2; 530/388.4; 530/388.5; 530/388.6
(58) Field of Search ............... 424/131.1, 138.1, 424/148.1, 160.1, 164.1, 151.1; 530/387.2, 387.7, 388.3, 388.35, 388.5, 388.6, 388.2, 388.4

(56) References Cited

U.S. PATENT DOCUMENTS

| | | | | |
|---|---|---|---|---|
| 4,908,203 A | * | 3/1990 | Thornton et al. | ............... 424/86 |
| 4,918,164 A | * | 4/1990 | Hellstrom et al. | ............... 530/87 |
| 5,053,224 A | | 10/1991 | Koprowski et al. | ......... 424/85.8 |
| 5,101,017 A | * | 3/1992 | Rubinstein et al. | .... 530/388.22 |

FOREIGN PATENT DOCUMENTS

| EP | 0141783 | * | 5/1985 | |
|---|---|---|---|---|
| EP | A-325 847 | | 8/1989 | ......... A61K/39/395 |

OTHER PUBLICATIONS

James N. Lowder, Richard A. Miller, Richard Hoppe & Ronald Levy.*

Suppression of Anti–Mouse Immunoglobulin Antibodies in Subhuman Primates Receiving Murine Monoclonal Antibodies Against T Cell Antigens.*

Letvin—The New England Journ. of Med. Nov. 4, 1993.*

Monestier et al. Cancer Res 49:123–126, 1989.*

Andibent Immunology Today 14:281–284, 1993.*

Klein et al, Antibody, Immunoconjugate & Radiopharmacesticals 1:55–64, 1988.*

Estabrook et al Cancer Immunol & Immunotherapy 23:143–147 1986.*

Haberman et al Cancer Immunol Immunotherapy 23:137–142, 1986.*

Haagensen et al ClinChem 26:1787–1790 1980.*

Riley Immunology Today 13:126–130, 1992.*

Barnes Research News May 6, 1988 pp. 719–721.*

Parkhouse et al Parasitology 99:S5–S19, 1999.*

Hoffman et al, Science 234:649–647, 1987.*

Butcher Parasitology 98:315–327 1989.*

Bloom Nature 342:115–120, 1989.*

Austin et al. "Human monoclonal anti–idiotypic antibody to the tumour–associated antibody 791T/36" *Immunology* 67:4 pp. 525–530 (Aug. 1989).

Bosslet et al. "Human monoclonal anti–idiotypic antibodies as an epitope vaccine against pancreatic carcinoma" *Behring Inst. Mitt.* vol. 82, pp. 193–196 (Apr. 1988).

\* cited by examiner

*Primary Examiner*—S. Devi
(74) *Attorney, Agent, or Firm*—Foley & Lardner

(57) ABSTRACT

A method of stimulating an immune response in a human against malignant cells or an infectious agent comprises the step of administering to the human an immunogenic amount of a primate anti-idiotype antibody or antibody fragment that acts as an immunogenic functional mimic of an antigen produced by or associated with a malignant cell or an infectious agent. Sub-human primate anti-idiotype antisera, especially from baboons, are preferred. Such anti-idiotype antibodies are used to make vaccines for inducing preventive immunity or a therapeutic immune response against tumors, viruses, bacteria, rickettsia, mycoplasma, protozoa, fungi and multicellular parasites.

26 Claims, No Drawings

VACCINES AGAINST CANCER AND INFECTIOUS DISEASES

This application is a continuation of application Ser. No. 07/470,637, filed Jan. 26, 1990 now abandoned.

BACKGROUND OF THE INVENTION

The present invention relates to a method of stimulating an immune response against malignant cells, pathogenic microorganisms, parasites or viruses in a patient using a primate "pseudoantigen" anti-idiotype antibody that acts as an immunogenic mimic of an antigen produced by or associated with a malignant cell, pathogenic microorganism, parasite or virus. A vaccine using such an anti-idiotype antibody is used in the foregoing method.

One of the major research goals in cancer, microbial or parasite therapy is to trigger the patient's immune system to actively respond to proliferation of the tumor or infectious agent. Certain pathologies, especially cancer and virus infections, appear to be resistant to the immune system because they exhibit characteristics that result in tolerance by the host or that disable the capability of the host's immune system to combat them.

The administration of anti-idiotype antibodies represents one of the most promising approaches to break the self-tolerance to tumor antigens. Anti-idiotype antibodies (termed Ab2) are antibodies directed against the variable region (antigen-binding site) of another antibody (Ab1), the idiotype, and some of these Ab2's (termed Ab2β) can mimic the three-dimensional structure of the antigen recognized by the Ab1. In turn, immunization with Ab2β antibodies can induce Ab3 antibodies with specificities similar to the original Ab1 antibodies (such Ab3 antibodies are called Ab1').

In a variety of experimental systems, Ab2β's have been able to induce specific immune responses in lieu of the original antigen. See, e.g., Nepom et al., Proc. Natl. Acad. Sci. USA, 81:2864–2867, 1984; Kennedy et al., Science (Wash., D.C.), 223:930–931, 1984; McNamara et al., Science (Wash., D.C.), 226:1325–1326, 1984; Grzych et al., Nature (Lond.), 316:74–76, 1985; Raychaudhuri et al., J. Immunol., 139:271–278, 1987; Dunn et al., Immunology, 60:181–186, 1987; Bhattacharya-Chatterjee et al., J. Immunol., 139:1354–1360, 1987; Viale et al., J. Immunol., 139:4250–4255, 1987; Smorodinsky et al., Eur. J. Immunol., 18:1713–1718; Kresina et al., J. Clin. Invest., 83:912–920, 1989; and Powell et al., J. Immunol., 142:1318–1324, 1989.

Various approaches using polyclonal or monoclonal Ab2 antibodies have been proposed for human therapy, but they all utilize immunoglobulins from foreign species, e.g., a mouse or goat, as immunogens. See, e.g., Herlyn et al., Proc. Natl. Acad. Sci. USA, 84:8055–8059, 1987; and Ferrone et al., 7th International Congress of Immunology (Abstract 117–9), Berlin, 1989.

Administration of such Ab2 molecules is likely to induce a strong immune response directed against the constant regions of the Ab2 molecule which would have no therapeutic value. Moreover, repeated immunization with foreign proteins can exert deleterious effects. Alternatively, administration of Ab2β molecules whose constant regions are identical or very similar to those of human immunoglobulins will induce an immune response restricted to idiotypic determinants. Antibodies obtained from animals such as monkeys, which are phylogenetically close to humans, can represent such an alternative. Indeed, baboon antibodies administered in cancer patients are less immunogenic than immunoglobulins from other animals.

In a variety of experimental systems, anti-idiotype antibodies have been shown to functionally mimic the antigen recognized by the Ab1 and to elicit a specific immune response in lieu of this original antigen. See, e.g., Bona et al., Ann. Immunol. (Paris), 136C:299–312, 1985. Furthermore, in two such systems, where the original antigens were the reovirus type 3 hemagglutinin and the random polymer GAT (glutamic acid, alanine and tyrosine), sequence analyses have shown homologies between these antigens and the complementary determining regions of the Ab2 molecules. See, Bruck et al., Proc. Notl. Acad. Sci. USA, 83:6578–6582, 1986; Ollier et al., EMBO J., 4:3681–3688, 1985.

Immunization with Ab2 antibodies mimicking microbial agents protected against challenges with the pathogenic agent in animal models and Ab2β antibodies would therefore represent valuable surrogate antigens when the original antigen (microbial or parasite) is not available for vaccination. The administration of a functional image antigen present on a foreign immunoglobulin molecule induced an immune response against a tolerized antigen in mice. Tumor antigens generally do not elicit a spontaneous immune response by the host. In a variety of animal models, immunization with Ab2 has been shown to prevent subsequent tumor growth. See, e.g., Raychaudhuri et al., supra; Dunn et al., supra; Powell et al., supra. In humans, clinical trials have shown that administration of murine Ab2 to cancer patients can induce tumor-binding Ab3 antibodies. It is necessary that the induced antibodies be therapeutically effective, but the beneficial effect of antibodies induced by murine Ab2 has not yet been shown. See Herlyn et al., supra; Ferrone et al., supra.

A need continues to exist for solutions to the problems noted above.

OBJECTS OF THE INVENTION

One object of the present invention is to provide a vaccine that will stimulate production of antibodies against normally tolerated tumor and viral antigens in human cancer patients and patients with normally intractable viral infections.

Another object of the invention is to provide a vaccine against pathogenic microorganisms and parasites.

Another object of the invention is to provide a method of treating cancer and infection by pathogenic microorganisms or parasites that uses a non-tumor and non-infectious agent to evoke an immune response specific to tumor or infectious agent antigens.

Another object of the invention is to induce immunity against the development of tumors and against the successful invasion of pathogenic microorganisms and parasites in healthy humans and animals.

Other objects of the invention will be apparent to those of ordinary skill in the art upon careful study of the following discussion and illustrative examples.

SUMMARY OF THE INVENTION

The foregoing objects are achieved by providing a method of stimulating an immune response in a human against malignant cells or an infectious agent, which comprises the step of administering to said human an immunogenic amount of a primate anti-idiotype antibody or antibody fragment that acts as an immunogenic functional mimic of an antigen produced by or associated with a malignant cell or an infectious agent. A method for preparing anti-idiotype antibodies and antibody fragments that mimic tumor or infectious agent antigens is provided, for use in the foregoing method and for preparing a vaccine therefor.

DETAILED DISCUSSION

Anti-idiotype antibodies that mimic tumor or infectious agent antigens are a safe and effective component of vaccines that can induce an immune response against cancers, pathogenic microorganisms, parasites and viruses, either as a therapy for patients suffering from malignancies or infections or as a preventive measure to repress the development of cancer or to ward off an invading microorganism, parasite or virus.

As used herein, "microbe" denotes virus, bacteria, rickettsia, mycoplasma, protozoa, fungi and like microorganisms, "parasite" denotes infectious, generally microsopic or very small multicellular invertebrates, or ova or juvenile forms thereof, which are susceptible to antibody-induced clearance or lytic or phagocytic destruction, e.g., malarial parasites, spirochetes and the like, while "infectious agent" or "pathogen" denotes both microbes and parasites.

Use of the term "antibody" herein will be understood to embrace whole antibodies, antibody fragments and subfragments and thus to be equivalent to the term "antibody/fragment" which is used interchangeably therefor in this discussion, unless otherwise noted. Antibodies can be whole immunoglobulin (IgG) of any class, e.g., IgG, IgM, IgA, IgD, IgE, chimeric antibodies or hybrid antibodies with dual or multiple antigen or epitope specifities, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex or by stimulating production of an anti-idiotype or anti-anti-idiotype antibody. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the invention.

The term "functionally mimic", as applied to an anti-idiotype antibody or antibody fragment with reference to an antigen or a specific epitope thereof, connotes the property of inducing production of a human antibody that specifically binds to that antigen/epitope and competitively inhibits binding to that antigen/epitope of the idiotype antibody or antibody fragment used to generate the anti-idiotype.

The idiotype antibodies or antibody fragments (Ab1) used to evoke an anti-idiotype antiserum (Ab2) can be polyclonal or monoclonal, the latter being preferred, whole immunoglobulin or fragments, or they can be more complex genetic constructs made by synthetic and/or recombinant techniques. The important feature which they require is an antigen-binding region that can be used to stimulate production of anti-idiotypes, at least a portion of which functionally mimic the original antigen.

Idiotype antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg U.S. Pat. Nos. 4,331,647, 4,348,376, 4,361, 544, 4,468,457, 4,444,744, 4,818,709 and 4,624,846. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used.

A wide variety of monoclonal antibodies against infectious disease agents have been developed, and are summarized in a review by Polin, in Eur. J. Clin. Microbiol., 3(5):387–398, 1984, showing ready availability. These include monoclonal antibodies (MAbs) against pathogens and their antigens such as the following:

Anti-bacterial Mabs
*Streptococcus agalactiae*
*Legionella pneumophilia*
*Streptococcus pyogenes*
*Escherichia coli*
*Neisseria gonorrhosae*
*Neisseria meningitidis*
Pneumococcus
*Hemophilis influenzae B*
*Treponema pallidum*
Lyme disease spirochetes
*Pseudomonas aeruginosa*
*Mycobacterium leprae*
*Brucella abortus*
*Mycobacterium tuberculosis*
Tetanus toxin
Anti-viral MAbs
Rabies virus
Influenza virus
Cytomegalovirus
Herpes simplex I and II
Human serum parvo-like virus
Respiratory syncytial virus
Varicella-Zoster virus
Hepatitis B virus
Measles virus
Adenovirus
Human T-cell leukemia viruses
Epstein-Barr virus
Murine leukiemia virus*
Mumps virus
Vesicular stomatitis virus
Sindbis virus
Lymphocytic choriomeningitis virus
Wart virus
Blue tongue virus
Sendai virus
Feline leukemia virus*
Reo virus
Polio virus
Simian virus 40*
Mouse mammary tumor virus*
Dengue virus
Rubella virus
* Animal virus
Anti-protozoan MAbs
*Plasmodium falciparum*
*Plasmodium vivax*
*Toxoplasma gondii*
*Trypanosoma rangeli*
*Trypanosoma cruzi*
*Trypanosoma rhodesiensei*
*Trypanosoma brucei*
*Schistosoma mansoni*
*Schistosoma japanicum*
*Babesia bovis*
*Elmeria tenella*
*Onchocerca volvulus*

*Leishmania tropica*
*Trichinella spiralis*
*Theileria parva*
*Taenia hydatigena*
*Taenia ovis*
*Taenia saginata*
*Echinococcus granulosus*
*Mesocestoides corti*
Antimycoplasmal MAbs
*Mycoplasma arthritidis*
*M. hyorhinis*
*M. orale*
*M. arginini*
*Acholeplasma laidlawii*
*M. salivarium*
*M. pneumoniae*

Additional examples of MAbs generated against infectious microorganisms that have been described in the literature are noted below.

MAbs against the gp120 glycoprotein antigen of human immunodeficiency virus 1 (HIV-1) are known, and certain of such antibodies can have an immunoprotective role in humans. See, e.g., Rossi et al., Proc. Natl. Acad. Sci. USA, 86:8055–8058, 1990. This shows that proper selection of the epitope can distinguish between a therapeutic and non-therapeutic target, and thereby permit selection of an anti-idiotype that evokes a therapeutic antibody response in the patient.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207:71–73, 1980).

Several groups have developed MAbs to *T. gondii,* the protozoan parasite involved in toxoplasmosis (Kasper et al., J. Immunol. 129:1694–1699, 1982; Id., 130:2407–2412, 1983).

MAbs have been developed against schistosomular surface antigens and have been found to act against schistosomulae in vivo or in vitro (Simpson et al. Parasitology, 83:163–177, 1981; Smith et al., Parasitology, 84:83–91, 1982; Gryzch et al., J. Immunol., 129:2739–2743, 1982; Zodda et al., J. Immunol. 129:2326–2328, 1982; Dissous et al., J. Immunol., 129:2232–2234, 1982).

*Trypanosoma cruzi* is the causative agent of Chagas' disease, and is transmitted by blood-sucking reduviid insects. A MAb has been generated that specifically inhibits the differentiation of one form of the parasite to another (epimastigote to trypomastigote stage) in vitro, and which reacts with a cell-surface glycoprotein; however, this antigen is absent from the mammalian (bloodstream) forms of the parasite (Sher et al., Nature, 300:639–640, 1982).

Suitable MAbs have been developed against most of the microorganisms (bacteria, viruses, protozoa, parasites) responsible for the majority of infections in humans, and many have been used previously for in vitro diagnostic purposes. These antibodies, and newer MAbs that can be generated by conventional methods, are appropriate for generating anti-idiotype antibodies for use in the method and vaccine of the present invention.

Polyclonal antibodies will normally be antiserum preparations from a variety of commonly used animals, e.g., goats, primates, donkeys, swine, rabbits, horses, hens, guinea pigs, rats or mice, and even human antisera after appropriate selection and purification. The animal antisera are raised by inoculating the animals according to a conventional protocol with an immunogenic form of the pathogen, e.g., whole tumor cells or crude or purified, live, attenuated or killed microbe or parasite, bleeding the animals and recovering serum or an immunoglobulin-containing serum fraction. Smaller antigenic structures, e.g., a more or less purified tumor antigen preparation, isolated tumor antigens and/or oligopeptide fragments thereof, or viral coat proteins and/or fragments thereof (such as the HIV-1 gp-120 peptide), microbial cell membrane or cell wall components, parasite surface antigens, portions thereof, or fragments resulting from destruction of the pathogen, also can be used to stimulate idiotype antibody production.

The antiserum is preferably affinity-purified by conventional procedures to, e.g., by binding antigen to a chromatographic column packing, e.g., Sephadex, passing the antiserum through the column, thereby retaining specific antibodies and separating out other immunoglobulins and contaminants, and then recovering purified antibodies by elution with a chaotropic agent, optionally followed by further purification, e.g., by passage through a column of bound blood group antigens or other non-pathogen species. This procedure may be preferred when isolating the desired antibodies from the serum of patients having developed an antibody titer against the pathogen in question.

Hybridoma-derived monoclonal antibodies (human, monkey, rat, mouse, or the like) are also suitable for use in producing anti-idiotypes and have the advantage of high specificity. They are readily prepared by what are now generally considered conventional procedures for immunization of mammals with an immunogenic antigen preparation, fusion of immune lymph or spleen cells, with an immortal myeloma cell line, and isolation of specific hybridoma clones. The hybridoma derived monoclonal antibodies are typically of murine or rat origin and typically are IgGs or IgMs, although suitable antibodies for use in preparing anti-idiotypes according to the invention are not intended to be limited as regards species or Ig class. More unconventional methods of preparing monoclonal antibodies are not excluded, such as interspecies fusions and genetic engineering manipulations of hypervariable regions, since it is primarily the antigen specificity of the antibodies that affects their utility in the present invention. Human lymphocytes can be fused with a human myeloma cell line to produce antibodies with particular specificities, preferably to epitopes which are not masked by circulating antibodies to the major antigenic sites on the pathogen.

The present invention also envisions the use of antigen-specific fragments as idiotypes and/or anti-idiotypes. Antibody fragments can be made by pepsin or papain digestion of whole immunoglobulins by conventional methods. It is known that antibody fragments may be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using papain produces two monovalent Fab fragments and an Fc fragment directly. These methods are described, inter alia, by Goldenberg, in U.S. Pat. Nos. 4,036,945 and 4,331,647 and references contained therein, which patents are incorporated herein in their entireties by reference, and in Nisonoff et al, Arch. Biochem. Biophys., 89, 230 (1960); Porter, Biochem. J., 73, 119 (1959); and Edelman et al, in "Methods in Immunology and Immunochemistry", Vol. 1, 422 (Acad. Press, 1967), and are conventional in the art.

Other methods of cleaving antibodies, such as separation of heavy chains to form monovalent light-heavy chain fragments, further cleavage of fragments, or other enzymatic, chemical or genetic techniques may also be used, so long as the fragments retain specificity to the pathogen or antigen against which their parent antibodies are raised.

It is not sufficient merely to evoke antibodies against the tumor or infectious agent antigen using an anti-idiotype antibody. A therapeutic response is required in order for the treatment to be successful, i.e., the antibodies must result in regression of the malignancy or repression, attenuation or destruction of the infectious agent. Careful selection of the tumor or infectious agent antigen and the epitope thereof which the anti-idiotype functionally mimics can enhance the efficacy of the therapeutic response, since not all tumor or infectious agent antigens will be equally effective targets for a therapeutic antibody response. Idiotype antibodies for later anti-idiotype production are preferably selected that bind to epitopes that are as specific as possible to the tumor or pathogen and non-crossreactive to normal human tissues. This will ensure that the eventual antibodies produced in response to challenge by an anti-idiotype that acts as a functional mimic of the epitope will act primarily on malignant cells or infectious agents rather than on healthy tissues. Another reason to select an epitope which is as tumor/pathogen-specific as possible is that immunization against a determinant found on normal cells could trigger a potentially harmful autoimmune response.

The idiotype antibody/fragment is used to generate anti-idiotypes by similar conventional methods as those used to generate the idiotypes themselves. An antigen-specific antibody, preferably a monoclonal antibody or antibody fragment, is injected into a mammal, advantageously in combination with an adjuvant. Immunizations are normally repeated periodically and the animal is bled several weeks post-injection to produce an antiserum. The antiserum is preferably adsorbed one or more times on an affinity column with bound normal immunoglobulin of the same isotype as the idiotype used for the immunization. This will remove anti-constant region components of the antiserum. Further adsorption on a column of bound idiotype can be effected, followed by chaotropic elution of the anti-idiotype. Confirmation of the specificity of the anti-idiotype antiserum is obtained by showing its capacity to compete with the antigen itself for idiotype antibody, e.g., in an ELISA assay.

Various parameters have to be considered when using Ab2 as therapeutic agents. For instance, monoclonal or polyclonal Ab2 can be administered to induce protective immunity. Monoclonal Ab2 antibodies have obvious practical advantages, such as their potentially unlimited supply and the convenience of their purification. However, Ab2β's that functionally mimic a tumor or pathogen antigen represent only a minority of the total Ab2 population.

Moreover, some but not all, Ab2β's (even if they can induce Ab1' antibodies) have protective effects against tumor or pathogen growth and, therefore, only a fraction of all monoclonal Ab2's have a potential therapeutic value. For instance, in an animal model, only one of two monoclonal Ab2's that functionally mimicked an antigen of the murine tumor, L1210/GZL, prevented tumor growth, even though both were able to induce Ab1' binding the original antigen. On the other hand, protective molecules are a part of the polyclonal Ab2 population, and the utilization of polyclonal Ab2 can sometimes be preferable. By circumventing the task involved in screening numerous monoclonal Ab2 antibodies, polyclonal Ab2 are particularly suitable when assessing the efficacy of idiotype based therapy.

The anti-idiotype antibody can be a whole antibody, antibody fragment, or subfragment. The anti-idiotype anti-serum can be enzymatically digested to form fragments, e.g., F(ab')$_2$ or Fab, using conventional techniques, as noted above in connection with idiotypes. Fragments are advantageously used instead of whole immunoglobulin because of the higher proportion of the molecule represented by the hypervariable region. Constant domains represent two-thirds of the IgG molecule and, therefore, most of the antigenic determinants on an immunoglobulin molecule are not idiotype-related. Administration of the Fab or F(ab')$_2$ fragments of the Ab2 molecule would diminish the magnitude of the response to the constant regions. Nevertheless, patients receiving F(ab')$_2$ fragments of murine IgG antibodies develop antibodies to the constant regions of mouse immunoglobulins. Past failures of murine anti-idiotypes that were able to induce an antibody response but could not be shown to result in a therapeutic benefit to the patient may have suffered from too great an immunogenicity of the constant region due to high interspecies variance that gave rise to a strong human anti-mouse antibody (HAMA) response and only a weak Ab1' response.

Another important parameter is the animal origin of the Ab2 antibody. The foreign nature of Ab2 molecules adds to their immunogenicity, but the production of antibodies to the constant regions of the Ab2 molecule is counterproductive.

The mammal chosen for production of the anti-idiotype will normally be a primate. It will be preferable to use a non-human primate immunoglobulin to reduce the possibility of an autoimmune response. An attractive approach is to utilize molecules phylogenetically close to human immunoglobulins.

In particular, baboon Ab2β antibodies or antibody fragments will be especially preferred. Baboon antibodies are normally well tolerated in humans and will share many common antigenic determinants, corresponding to regions of high homology to human immunoglobulin. This is shown by the fact that commercially available anti-human antisera also bind baboon antibodies. Therefore, the hypervariable regions of baboon antibodies or antibody fragments will normally provoke the bulk of the immune response, resulting in the best yield of antibodies which bind to the desired antigen.

Because of the high homology to human immunoglobulin, baboon antiserum is normally very weakly immunogenic in humans. In a study of patients treated with anti-tumor antibodies from various animal species, baboon immunoglobulins were the least immunogenic. Only one of 66 patients receiving baboon antibodies developed anti-baboon antibodies whereas, for instance, 36% of patients treated with cynomolgus monkey immunoglobulins produced anti-antibodies. See, Klein et al., supra. In another study, 9 of 14 patients having received an infusion of baboon anti-CEA antibodies developed anti-baboon antibodies, but most of the antibody titers were minimally above the sensitivity limit of the assay utilized. See, Huberman et al., Cancer Immunol. Immunother., 23:137–142, 1986. None of four patients treated with baboon anti-gross cystic disease fluid protein-15 antibody produced human anti-baboon antibodies, even though one of these patients received four antibody infusions. See, Estabrook et al., Cancer Immunol. Immunother., 23:143–147, 1986.

In order to overcome the weak immunogenicity of primate anti-idiotype antibodies or fragments, especially baboon Ab2β, in human recipients, the immunoglobulins are preferably made more immunogenic by administration in a vaccination vehicle. Typically, they are injected in combination with an adjuvant such as Freund's complete or incomplete adjuvant, alum, or the like. Furthermore, their immunogenicity can be increased by coupling to an immunogenic carrier known to be safe in humans, e.g., an attenuated microbial agent such as tetanus toxoid, Bacillus Calmette-Guerin (BCG) or the like.

The antigen which the anti-idiotype mimics can be used in a vaccination protocol in conjunction with the antibody. The antigen can be administered with the anti-idiotype or separately, either concurrently or sequentially. Often, the anti-idiotype immunogen will stimulate an immune response, and sensitize the patient to the antigen itself, after which the antigen can be used for further antibody induction.

It is primarily the non-homologous regions of the anti-idiotype, especially the hypervariable region, that induce complementary antibody production. Administration of preferred baboon Ab2 antiserum results in less anti-constant region antibody production than immunization with Ab2 from more common sources, such as goat or mouse.

The utility of baboon antiserum for generation of antigen-specific antibodies can be shown in a mouse model system. Mice immunized with baboon Ab2 antibodies against a murine monoclonal antibody that specifically binds to the colorectal cancer marker carcinoembryonic antigen (CEA) develop Ab3 antisera containing at least some antibodies of the Ab1' type and, therefore, bind the CEA epitope recognized by NP-4. NP-4 is chosen since it is specific for high molecular weight CEA, it does not react with the normal cross-reactive antigen present on granulocytes or with low molecular weight CEA variants, such as meconium antigen. Generation of Ab1' as part of the AB3 antisera can be shown by demonstrating that the Ab3 sera inhibit subsequent recognition of CEA by biotinylated NP-4 in a competitive ELISA. Control sera from mice immunized with normal baboon immunoglobulins do not inhibit this binding. The inhibition is selective since none of the sera from either group are able to inhibit the binding between NP-3 and CEA. This indicates that Ab2-induced mouse anti-CEA antibodies are specific for the epitope recognized by NP-4.

These results are not related to a possibly weak immunogenicity of the normal baboon immunoglobulins, since sera from both groups contain very high titers of mouse anti-baboon antibodies. Furthermore, Ab3 antibodies share idiotypes with Ab1 (NP-4) antibodies since sera from mice immunized with baboon Ab2 inhibit the binding between NP-4 and baboon Ab2 antibodies. Experiments such as these provide further evidence that baboon anti-NP-4 Ab2 antibodies functionally mimic a CEA epitope and that they can induce Ab1' antibodies to this particular CEA epitope. Only anti-CEA antibodies to the NP-4 epitope, and not to the non-crossreacting NP-3 epitope, are induced. Moreover, no anti-CEA antibodies are induced by injection of normal baboon immunoglobulins.

Anti-idiotype Ab2β antibodies can serve as surrogate antigens and have further advantages of ease of production and often greater safety. An important further advantage of judiciously selected Ab2β antibodies in an appropriate vaccine formulation is that it can be used to break tolerance to self-antigens. Thus, even those tumor and infectious agent antigens that are normally not immunogenic ("tolerized" antigens) can be mimicked, and antibodies that specifically bind to such antigens can be induced.

In summary, primate, preferably sub-human primate, and especially baboon anti-idiotype antibodies can functionally mimic a tumor or pathogen antigen epitope recognized by a specific idiotype antibody. Their use as a vaccine/immunogen induces the production of anti-anti-idiotype antibodies, at least a portion of which will have a protective/therapeutic affect if the antigen epitope is well selected.

To illustrate the method of the invention, a description is provided for the production and purification of baboon Ab2 antibodies mimicking an epitope on carcinoembryonic antigen (CEA), a marker secreted by certain types of colorectal tumors and by other types of cancer, and their ability to induce production of therapeutic anti-CEA antibodies that cause regression of CEA-producing cancers. A description is also provided for production of anti-idiotype antibodies mimicking the gp-120 viral coat glycoprotein component of human immunodeficiency virus HIV-1, implicated in AIDS, and use thereof to confer immunity against infection by the AIDS virus.

It will be appreciated that these examples are illustrative and not limitative in any way of the scope of the invention, which is defined by the appended claims.

EXAMPLE 1

Baboon Anti-tumor Ab2 Antibody Preparation

An adult female baboon is repeatedly immunized with 1 mg of NP-4 emulsified in Freund's incomplete adjuvant (total volume 1 ml/injection). NP-4 is a BALB/c $IgG_1k$ murine monoclonal antibody which recognizes an epitope on the CEA molecule which is not shared with either non-specific crossreacting antigen or with meconium antigen. Injections are performed s.c. at 4 different sites in the axillary areas and the animal is bled two weeks after each immunization. Anti-NP-4 antibodies are purified by affinity chromatography: sera are adsorbed on an NP-4-AFFI-Gel column (Bio-Rad, Richmond Calif.) and specific antibodies are eluted by 0.1 M glycine-HC1, pH 2.5. The resultant preparation contains both anti-idiotype antibodies and antibodies directed to the constant regions of the NP-4 molecule.

The preparation is made idiotype-specific by absorption of the anti-constant region antibodies on an NP-3-Affi-Gel column. NP-3 is a BALB/c $IgG_1k$ murine monoclonal antibody which does not crossblock NP-4 and which recognizes an epitope on the CEA molecule which is not shared with non-specific crossreacting antigen but which is also present on meconium antigen. NP-3 is chosen as an adsorbent since it has the same isotype ($IgG_1k$) as NP-4 and it is an anti-CEA antibody not cross-reacting with NP-4. Two adsorption steps on NP3-AFFI-Gel are normally sufficient to remove all of the detectable anti-constant region antibodies.

EXAMPLE 2

Specificity of Baboon Ab2 Antibodies

The binding of baboon Ab2 antibodies to murine monoclonal antibodies is tested in ELISA. Briefly, polyvinyl microtitration plates are coated overnight (50 ul/well) with one of NP-4, NP-3 or Mu-9 (10 ug/ml in carbonate buffer, pH 8.6). Mu-9 is a monoclonal $IgG_1k$ antibody directed against colon-specific antigen-p. Following post-coating with bovine serum albumin (BSA) (1% in phosphate-buffered saline (PBS) containing 0.05% TWEEN-20), baboon Ab2, diluted at varying concentrations in PBS-BSA-Tween, is added (50 ul/well) for 2 hours at room temperature. After washing, peroxidase-conjugated mouse anti-human immunoglobulin IgG (Jackson Immunoresearch, West Grove, Pa., 1/10,000 in PBS-BSA-Tween) is added for 2 hours at room temperature. In pilot experiments, it is determined that commercially available anti-human immunoglobulin reagents are suitable for the detection of baboon antibodies. After extensive washings, 100 ul of substrate (o-phenylene-diamine 0.4 mg/ml, $H_2O_2$ 0.012% in citrate-phosphate buffer, pH 5) is added to each well and the optical density is read after 20 minutes at 450 nm using a kinetic microplate reader (Molecular Devices, Palo Alto, Calif.).

The assays confirm that baboon Ab2 reacts only with NP-4 and not with the isotype-matched control antibodies, NP-3 or Mu-9. Similarly, baboon Ab2 shows virtually no binding when tested against other irrelevant monoclonal antibodies of various isotypes. Thus, the Ab2 antibodies are specific for NP-4.

EXAMPLE 3
Inhibition of Binding to CEA by Baboon Ab2 Antibodies

Anti-idiotype antibodies are directed against determinants in the variable regions of the antibody molecule, but these idiotypic determinants may or may not be located within the antigen-combining site of the antibody molecule. By definition, an Ab2 molecule that functionally mimics the original antigen must recognize a determinant within the antigen combining site and, therefore, should inhibit the binding between Ab1 and the original antigen.

A competitive ELISA is used to determine whether the baboon Ab2 antibodies bind to a determinant located within the combining site of NP-4. The competitive ELISA is conducted as follows: baboon sera diluted 1/10 in PBS-BSA-Tween are added (50 ul/well) for 2 hours onto CEA-coated polyvinyl chloride microtitration plates. After washing, biotinylated NP-4 (0.025 ug/ml) is added onto the plates for 30 minutes, followed by streptavidin-peroxidase (0.05 ug/ml) for one hour. The reaction is revealed by addition of substrate as described for Example 2. Biotinylated anti-CEA NP-3 is used as one control, while preincubation with normal baboon immunoglobulins is used as a further check.

Preincubation with baboon Ab2 inhibited virtually completely binding of NP-4 to CEA. Baboon Ab2 did not affect the binding of NP-3 to CEA and normal baboon immunoglobulins did not inhibit the binding of NP-4 to CEA. The assays show that this inhibition is specific.

EXAMPLE 4
Cancer Therapy

A 40-year old female patient with a recurrent tumor of the ascending colon and metastases to multiple lobes of the left lung and multiple sites in the liver has an elevated CEA titer. She is injected I.D. in the left buttock with a mixture of 1 mg of baboon Ab2 CEA-mimicking antibody produced according to Example 1, in an adjuvant preparation containing 0.1 ml BCG (Litton Bionetics). Immunization is repeated at weekly intervals for three weeks. The BCG is omitted for the third injection. A 50 ml sample of whole blood is withdrawn prior to beginning of treatment, one week after each injection and monthly thereafter, and CEA titers are determined. Six weeks later, the patient is tested for reactivity to both CEA and baboon Ab2. A significantly high level of reaction is found.

After an induction period of 6–20 weeks following the completion of the immunization protocol, the patient's CEA titer is significantly reduced and a partial regression of the tumors is observed.

Another patient is given baboon Ab2 antibody vaccine in a similar immunization protocol, except that the third injection is purified CEA instead of Ab2. Titers of anti-CEA antibodies were comparable in the two patients and partial tumor regression also was observed in the second patient.

EXAMPLE 5
Baboon Anti-HIV-1 Ab2 Antibody Preparation

Pristane-primed Balb/c mice are repeatedly immunized with human immunodeficiency virus 1 (HIV-1) envelope glycoprotein gp120, in complete Freund's adjuvant. After several weeks, the mice are sacrificed, their spleens are excised, and spleen cells are removed and washed. Fusion of the spleen cells with murine myeloma cells is effected and resultant hybridomas are selected and cloned for production and secretion of monoclonal anti-HIV-1 antibodies that specifically bind to gp120.

The monoclonal anti-HIV-1 idiotype antibodies are used to immunize baboons to produce Ab2 antibodies, according to the procedure of Example 1. The antiserum is further purified by adsorption on a column with bound antibody of the same isotype as the Ab2 but different specificity. The immunospecificity of the affinity purified Ab2 preparation is confirmed by analogous procedures to those of Examples 2 and 3.

EXAMPLE 6
AIDS Immunity

A test group of 20 male intravenous drug users who test negative for HIV-1 antibodies are divided into two paired subgroups. The members of the first subgroup are each immunized with the affinity purified Ab2 preparation according to Example 5, using a similar immunization protocol as in Example 4, except that booster injections of gp120 are given at four-month intervals during the test period. The members of the second subgroup are not given injections.

The members of each group are followed for three years and tested periodically for anti-HIV serum antibodies and development of ARC and AIDS symptoms. After three years, seven members of the second group are seropositive, and two develop early symptoms of AIDS. One member of the first group becomes seropositive within two weeks of the end of the immunization schedule, suggesting that he is undetectably infected at the start of the trial. The remaining members of the first group develop anti-HIV antibodies within 620 weeks after the end of the immunization schedule, but do not develop AIDS symptoms during the three year period of observation. Their antibody titers remain elevated throughout the test period.

EXAMPLE 7

Antiviral Therapy

Murine monoclonal antibodies are raised to cytomegalovirus (CMV) coat protein and used to immunize a baboon. Ab2 antiserum is withdrawn, purified and tested for specificity analogously to the procedures of Examples 1–3. A three-year old male patient with a diagnosis of early-stage cytomegalic inclusion disease is given injections of the baboon Ab2 antiserum using a protocol similar to that of Example 4. After 8 weeks from the end of the immunization schedule, the patient has developed a high titer of anti-CMV antibodies and his symptoms are significantly less severe.

EXAMPLE 8

Antimalarial Therapy

Murine monoclonal antibodies against merozoites and sporozoites of Plasmodium falciparum are made by the procedure of Example 6 of U.S. patent application Ser. No. 07/399,566 now abandoned. Briefly, splenocytes from hyperimmunized mice are fused with myeloma cells and hybridomas secreting specific antibodies are selected and cloned. The antibodies are of the $IgG_1$ subclass. A mixture of anti-merozoite and anti-sporozoite antibodies are injected into a baboon and Ab2 antiserum is withdrawn, purified and screened for specificity as in Examples 1–3 herein.

A 37-year old female patient suffering from fairly early stage *P. falciparum* malaria and exhibiting mild chills and fever is injected with the baboon antiserum according to an analogous immunization protocol to that of Example 4 herein. The presence of merozoites in the patient's blood is detectable at the start of the treatment. Within two weeks after the end of the immunization schedule, the patient's anti-merozoite antibody titer is high, and within another week, the presence of merozoites in her blood is no longer detectable. The disease does not progress to the mature erythrocytic stage, the patient's fever subsides and further disease symptoms do not occur. Periodic booster injections of Ab2 antiserum at three-month intervals for one year maintain the anti-merozoite antibody titer and the patient is free of symptoms for that time, without recurrence thereafter when the booster injections are discontinued.

It will be readily apparent to one of ordinary skill in the art that many variations and modifications may be made without departing from the spirit and scope of the invention. For example, analogous antisera against idiotypes specific to therapeutically sensitive epitopes on other tumor or pathogen antigens can be prepared and used to provide preventive immunity or a therapeutic immune response using procedures analogous to those of the preceding examples. Antibody fragments and/or antibody-like constructs also can be used to mimic antigen in a vaccine to raise antibodies for therapeutic and preventive use.

All publications and patent applications cited in this specification are incorporated in their entireties herein by referenceas as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the invention, as defined by the appended claims.

What is claimed is:

1. A method of stimulating an immune response in a human against malignant cells or an infectious agent, which comprises the step of administering to said human an immunogenic amount of a baboon anti-idiotype antibody or antibody fragment that acts as an immunogenic functional mimic of an antigen that is a marker for a malignant cell or an infectious agent.

2. The method of claim 1, wherein said baboon anti-idiotype antibody or antibody fragment is an immunogenic functional mimic of an epitope on said antigen.

3. The method of claim 1, wherein said antigen is a marker for a malignant cell.

4. The method of claim 3, wherein said antigen is carcinoembryonic antigen.

5. The method of claim 4, wherein said baboon anti-idiotype antibody or antibody fragment acts as an immunogenic mimic of an epitope on carcinoembryonic antigen which is not shared with either nonspecific crossreacting antigen or meconium antigen.

6. The method of claim 1, wherein said antigen is a marker for a virus.

7. The method of claim 6, wherein said antigen is a human immunodeficiency virus envelope protein.

8. The method of claim 7, wherein said envelope protein is gp120.

9. The method of claim 1, wherein said antigen is a marker for an infectious microorganism selected from the group consisting of bacteria, rickettsia, mycoplasma, protozoa and fungi.

10. The method of claim 1, wherein said antigen is a marker for an infectious parasite.

11. The method of claim 1, wherein said baboon anti-idiotype antibody or antibody fragment is administered in combination with an immunostimulant adjuvant.

12. The method of claim 11, wherein said adjuvant is at least one member selected from the group consisting of Freund's adjuvant, alum, Bacillus Calmette-Guerin and tetanus toxoid.

13. The method of claim 1, further comprising the administration of said antigen.

14. The method of claim 1, wherein said human is a cancer patient suffering from a malignant solid tumor or hematopoietic neoplasm.

15. The method of claim 14, wherein said malignant solid tumor or hematopoietic neoplasm is a gastrointestinal, lung, breast, prostate, ovarian, testicular, brain or lymphatic lesion, a sarcoma or a melanoma lesion.

16. The method of claim 1, wherein said human is suffering from a viral infection.

17. The method of claim 1, wherein said human is suffering from infection by an infectious microorganism selected from the group consisting of bacteria, rickettsia, mycoplasma, protozoa and fungi.

18. The method of claim 1, wherein said human is suffering from infection by an infectious parasite.

19. The method of claim 1, wherein said human is not suffering from a malignancy or from an infection, and said immune response results in immunity against the development of malignancy by a cell having said malignant cell marker, or against infection by an infectious agent having said infectious agent marker.

20. An antitumor or antipathogen vaccine, comprising an immunogenic amount of a baboon anti-idiotype antibody or antibody fragment that is an immunogenic functional mimic of an antigen that is a marker for a malignant cell or infectious agent, and a physiologically acceptable vaccine vehicle.

21. The vaccine of claim 20, wherein said vehicle comprises an effective amount of an immunostimulant adjuvant.

22. The vaccine of claim 21, wherein said adjuvant is at least one member selected from the group consisting of Freund's adjuvant, alum, Bacillus Calmette-Guerin and tetanus toxoid.

23. The vaccine of claim 20, which further comprises said antigen.

24. The vaccine of claim 22, which further comprises said antigen.

25. The method of claim 1, wherein said antigen is carcinoembryonic antigen.

26. The method of claim 1, wherein said baboon anti-idiotype antibody or antibody fragment acts as an immunogenic mimic of an epitope on carcinoembryonic antigen which is not shared with either nonspecific cross-reacting antigen or meconium antigen.

* * * * *